(12) United States Patent
Shvartsman et al.

(10) Patent No.: US 10,132,888 B2
(45) Date of Patent: Nov. 20, 2018

(54) SELF-SHIELDED SPLIT GRADIENT COIL

(71) Applicant: VIEWRAY TECHNOLOGIES, INC., Mountain View, CA (US)

(72) Inventors: Shmaryu M. Shvartsman, Highland Heights, OH (US); Gordon D. Demeester, Wickliffe, OH (US); John L. Patrick, Chagrin Falls, OH (US); James F. Dempsey, Chagrin Falls, OH (US)

(73) Assignee: ViewRay Technologies, Inc., Oakwood Village, OH (US)

( * ) Notice: Subject to any disclaimer, the term of this patent is extended or adjusted under 35 U.S.C. 154(b) by 889 days.

(21) Appl. No.: 14/550,464

(22) Filed: Nov. 21, 2014

(65) Prior Publication Data

US 2015/0077118 A1    Mar. 19, 2015

Related U.S. Application Data

(63) Continuation of application No. 12/951,976, filed on Nov. 22, 2010, now Pat. No. 8,896,308.
(Continued)

(51) Int. Cl.
*G01R 33/38* (2006.01)
*G01R 33/385* (2006.01)
(Continued)

(52) U.S. Cl.
CPC ....... *G01R 33/3806* (2013.01); *G01R 33/385* (2013.01); *G01R 33/3856* (2013.01);
(Continued)

(58) Field of Classification Search
CPC .............. G01R 33/385; G01R 33/4215; G01R 33/3856; G01R 33/3806; G01R 33/3858;
(Continued)

(56) References Cited

U.S. PATENT DOCUMENTS 5,365,927 A    11/1994   Roemer et al.
5,378,989 A    1/1995    Barber et al.
(Continued)

FOREIGN PATENT DOCUMENTS

JP    H07-213507 A    8/1995
JP    2009-112870 A   5/2009
(Continued)

OTHER PUBLICATIONS

English translation of WO 2009/099001 A1 provided by Espacenet. 11 pages.*
(Continued)

*Primary Examiner* — Rishi Patel
(74) *Attorney, Agent, or Firm* — Pillsbury Winthrop Shaw Pittman LLP

(57) ABSTRACT

Gradient coil assemblies for horizontal magnetic resonance imaging systems (MRIs) and methods of their manufacture. Some embodiments may be used with open MRIs and can be used with an instrument placed in the gap of the MRI. In general, concentrations of conductors or radially oriented conductors may be moved away from the gap of the MRI so as to reduce eddy currents that may be induced in any instrument placed within the gap. Systems for directly cooling primary gradient and shield coils may be utilized and various coil supporting structures may be used to assist in coil alignment or to facilitate use of an instrument in the MRI gap.

20 Claims, 10 Drawing Sheets

Related U.S. Application Data

(60) Provisional application No. 61/263,280, filed on Nov. 20, 2009.

(51) Int. Cl.
  *G01R 33/421* (2006.01)
  *G01R 33/48* (2006.01)
  *A61N 5/10* (2006.01)

(52) U.S. Cl.
  CPC ..... *G01R 33/3858* (2013.01); *G01R 33/4215* (2013.01); *G01R 33/4808* (2013.01); *A61N 2005/1055* (2013.01)

(58) Field of Classification Search
  CPC .............. G01R 33/4808; G01R 33/421; A61N 2005/1055
  USPC ................................................. 324/300–322
  See application file for complete search history.

(56) References Cited

U.S. PATENT DOCUMENTS

| | | |
|---|---|---|
| 5,585,724 A | 12/1996 | Morich et al. |
| 5,952,830 A | 9/1999 | Petropoulos et al. |
| 6,236,203 B1 | 5/2001 | Shvartsman et al. |
| 6,311,389 B1 | 11/2001 | Uosaki et al. |
| 6,591,127 B1 | 7/2003 | McKinnon |
| 6,940,281 B2 | 9/2005 | Feenan et al. |
| 7,489,131 B2 | 2/2009 | Lvovsky |
| 8,334,697 B2 | 12/2012 | Overweg et al. |
| 8,378,677 B2 | 2/2013 | Morich et al. |
| 8,896,308 B2 | 11/2014 | Shvartsman et al. |
| 2003/0197507 A1 | 10/2003 | Liu |
| 2004/0239327 A1 | 12/2004 | Heid et al. |
| 2005/0030028 A1* | 2/2005 | Clarke ............... G01R 33/3403 324/318 |
| 2005/0197564 A1 | 9/2005 | Dempsey |
| 2006/0033496 A1 | 2/2006 | Shvartsman et al. |
| 2009/0299170 A1* | 12/2009 | Gebhardt ............... A61B 5/055 600/411 |
| 2010/0033186 A1* | 2/2010 | Overweg ............... A61B 5/055 324/318 |
| 2010/0188082 A1* | 7/2010 | Morich ............... G01R 33/3806 324/307 |
| 2010/0321019 A1* | 12/2010 | Imamura ............... G01R 33/385 324/318 |
| 2011/0087090 A1* | 4/2011 | Boernert ............... A61B 5/055 600/411 |

FOREIGN PATENT DOCUMENTS

| | | | | |
|---|---|---|---|---|
| JP | WO 2009099001 A1 * | 8/2009 | .......... | G01R 33/385 |
| WO | WO-03/008986 A2 | 1/2003 | | |
| WO | WO-2008/122899 A1 | 10/2008 | | |
| WO | WO-2009/004521 | 1/2009 | | |
| WO | WO-2009/107005 A2 | 9/2009 | | |

OTHER PUBLICATIONS

Extended European Search Report and supplementary European Search Opinion of European Patent application No. EP 10822326. 2-1560, dated Aug. 2, 2013.

Green et al. "Split cylindrical gradient coil for combined PET-MR system." Proc. Intl. Soc. Mag. Reson. Med. 16 (2008):352.

International Search Report of PCT/US2010/057650 dated Feb. 2, 2011.

Lagendijk J. J. et al. "MRI guided radiotherapy: A MRI based linear accelerator." Radiotherapy & Oncology. vol. 56, No. Supplement 1. Sep. 2000. (Sep. 2000):S60-S61. XP008012866. 19th Annual Meeting of the European Society for Therapeutic Radiology and Oncology. Istanbul, Turkey; Sep. 19-23, 2000.

Lucas et al. "Simultaneous PET-MR: toward a combined microPET®-MR system." Proc. Intl. Soc. Mag. Reson. Med. 15(2007):922.

Overweg et al. "System for MRI guided Radiotherapy." Proc. Intl. Soc. Mag. Reson. Med. 17(2009):594.

Shvartsman et al. "Gradient Coil Induced Eddy Current Computation Using the Boundary Elements Method." Proc. Intl. Soc. Mag. Reson. Med. 17(2009):3055.

Tamada and Kose. "Two-Dimensional Compressed Sensing Using the Cross-sampling Approach for Low-Field MRI Systems." IEEE Transactions on Medical Imaging. vol. 33, No. 9. Sep. 2014. pp. 1905-1912.

\* cited by examiner

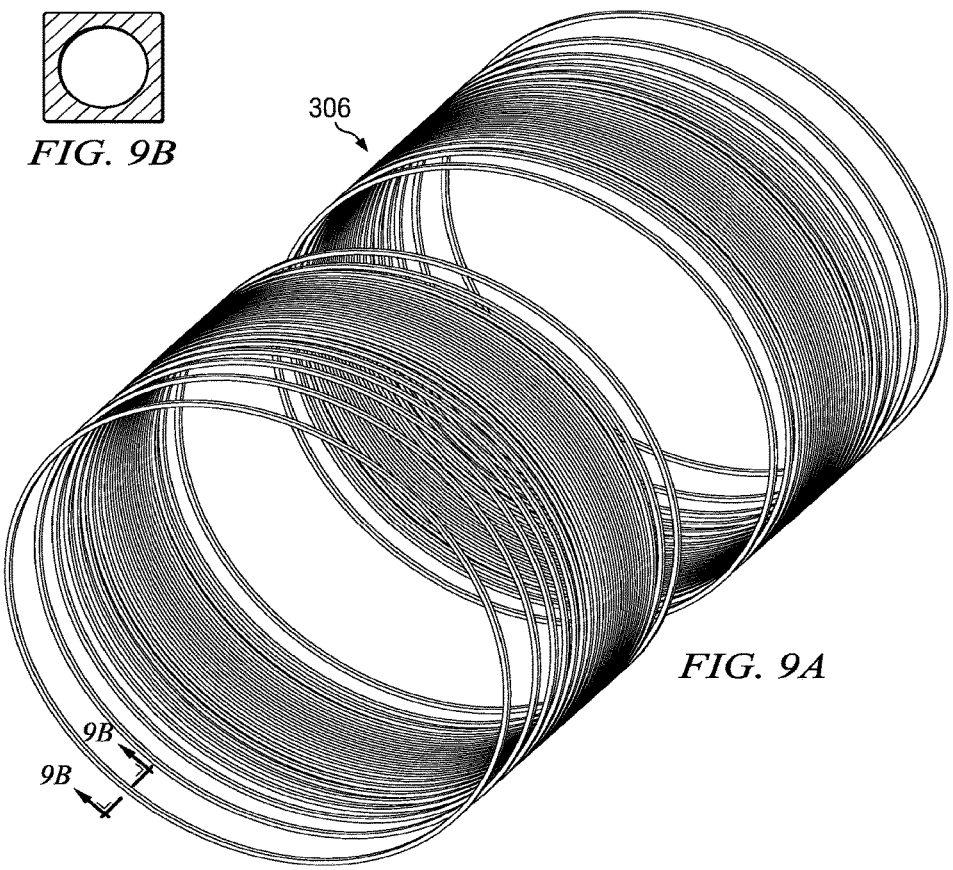
FIG. 9B
FIG. 9A
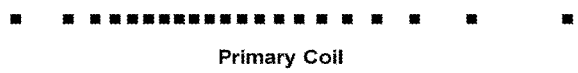
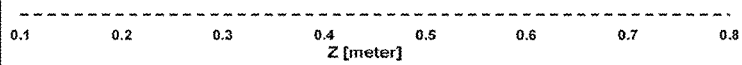
FIG. 9C

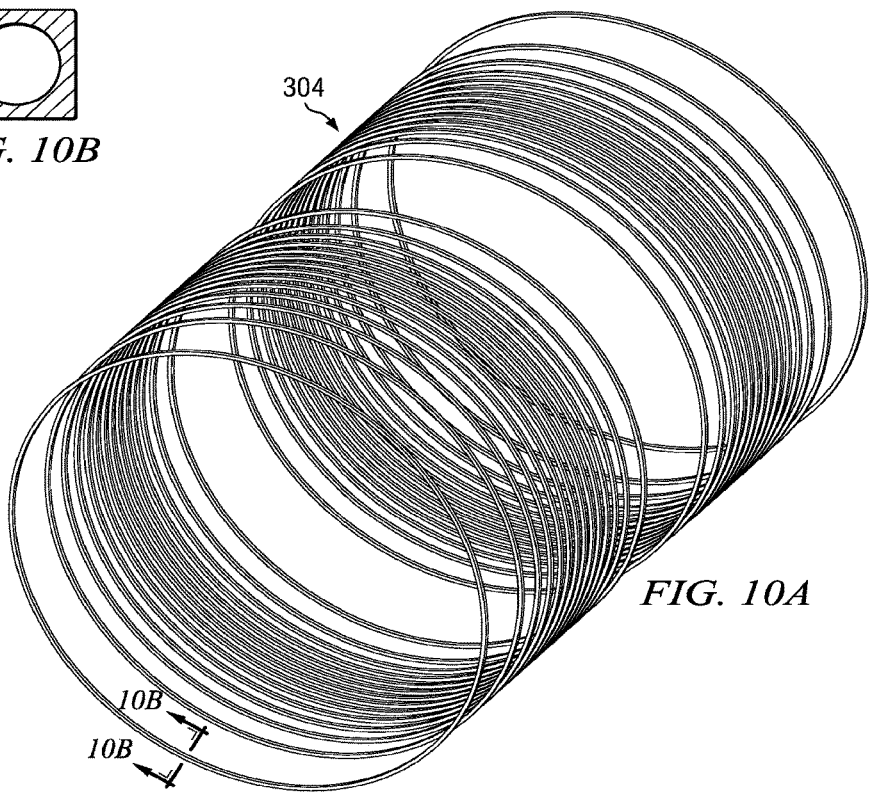
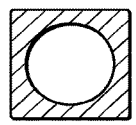
FIG. 10B
FIG. 10A
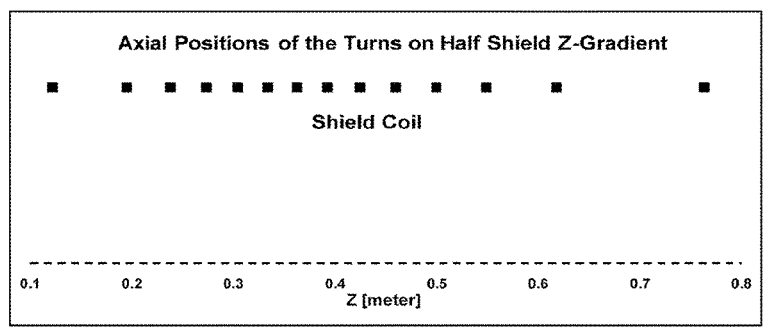
FIG. 10C

SELF-SHIELDED SPLIT GRADIENT COIL

RELATED APPLICATION

This patent application is a continuation of and claims the benefit of priority under 35 U.S.C. § 120 of U.S. patent application Ser. No. 12/951,976, entitled "Self-Shielded Gradient Coil", filed Nov. 22, 2010, which claims the benefit of priority of U.S. Provisional Patent Application No. 61/263,280, filed Nov. 20, 2009, entitled "Self-Shielded Split Gradient Coil". The disclosures of each document mentioned in this paragraph are incorporated herein by reference in their entirety.

BACKGROUND

1. Technical Field

The present application relates to systems and methods for magnetic resonance imaging ("MRI") and particularly to gradient coil assemblies and methods for their manufacture and use with magnetic resonance imaging systems.

2. Related Art

Magnetic resonance imaging, or nuclear magnetic resonance imaging, is primarily a medical imaging technique used most commonly in radiology to visualize the internal structure and function of the body. MRI is described, for example, by E. MARK HAACKE ET AL., MAGNETIC RESONANCE IMAGING: PHYSICAL PRINCIPLES AND SEQUENCE DESIGN (Wiley-Liss 1999), which is hereby incorporated by reference. The present disclosure relates to the magnetic resonance arts and specifically to horizontal (solenoid magnet) MRIs. It finds particular application in conjunction with medical magnetic resonance imaging and will be described with particular reference thereto. It is to be appreciated, however, that the disclosure also finds application in conjunction with other types of magnetic resonance imaging systems, magnetic resonance spectroscopy systems, and the like.

In magnetic resonance imaging, linear magnetic field gradients are used for spatial encoding. Gradient coils are used to produce these linear magnetic field gradients. Typical horizontal MRIs have horizontal cylindrical gradient coil assemblies that span the length of the device. Horizontal "open" MRIs have been developed for claustrophobic patients. Open MRIs have a split main magnet with a gap in the center and typically have split gradient coils as well to provide a clear opening for the patient. More recently, it has become desirable to include various treatment and imaging modalities in combination with MRIs and open MRIs, such as radiation therapy devices, biopsy needles, ablation devices, surgical devices, ultrasound, PET, SPECT, CT and others. For example, it would be desirable to place such instruments in the gap region of an open MRI. However, problems exist with this placement because of interference from various magnetic fields associated with the operation of the MRI as well as the problem of heating conductors the vicinity of the gradient coil.

Thus, there exists a need for improved MRI gradient coil assemblies and methods of manufacturing MRI gradient coil assemblies. There further exists a need for improved gradient coil assemblies for horizontal open MRIs, and gradient coil assemblies that allow for operation of a horizontal open MRI in conjunction with additional medical devices.

SUMMARY

Gradient coil assemblies and methods for their manufacture and use within horizontal MRIs are disclosed. Some embodiments may be used in conjunction with an open MRI and an instrument placed within its gap. Embodiments of the gradient coil assemblies disclosed herein may include primary gradient coils and shielding coils, and may also include electrical connections between the primary gradient and shielding coils that may be arranged to be a sufficient distance from the open MRI gap so as to reduce eddy currents that may be induced in any instrument that is placed within the gap.

In some embodiments, the primary gradient coils and shielding coils may be formed as substantially cylindrical conductors.

In still further embodiments, the conductors in the assembly are arranged so that any concentration of conductors oriented in a radial direction are located at least 5 centimeters from the gap of the open MRI.

In further embodiments, the electrical connections or conductors connecting the primary gradient and shield coils may be located at least 5 centimeters from the gap or can be located at the outer ends of the MRI.

In some embodiments, each of the primary gradient coils may be directly cooled and each may also be a hollow conductor.

In some embodiments, the gradient coil assembly may be mounted at both the outer ends and the gap-facing ends of the MRI.

In further embodiments of the present disclosure, used in conjunction with an open MRI, the gradient coil assemblies disclosed herein may include a supporting structure that contains all of the primary gradient coils and shielding coils and has a portion that traverses the gap of the open MRI so that alignment of the coils is facilitated.

In some embodiments, the portion of the supporting structure traversing the gap may be a portion of an inner former.

In further embodiments, the portion of the supporting structure traversing the gap may have a radiation attenuation value that is uniform across the structure and may also have a radiation attenuation value that is less than five percent for a Cobalt 60 gamma radiation beam.

In some embodiments of the present disclosure, used in conjunction with an open MRI and a radiation beam aimed through the gap of the open MRI, the gradient coil assemblies disclosed herein may have at least one of the primary gradient coils traversing the gap of the open MRI, that at least one coil having a first radiation attenuation value and the assembly also including a supporting structure that traverses the gap and has a second radiation attenuation value substantially equivalent to the first radiation attenuation value such that attenuation of the radiation beam will be substantially uniform as it passes through the supporting structure and at least one gradient coil that traverse the gap.

In some embodiments, the at least one primary gradient coil traversing the gap may be aluminum. In still further embodiments, the portion of the supporting structure that traverses the gap may be impregnated with alumina.

These and other features, aspects, and advantages of the present disclosure will become better understood with reference to the following description and claims.

BRIEF DESCRIPTION OF THE DRAWINGS

Features, aspects, and embodiments of the disclosure are described in conjunction with the attached drawings, in which:

FIG. 9A shows a simplified layout of an embodiment of a Z gradient primary coil;

FIG. 9B shows a cross sectional view an embodiment of a conductor used with the embodiment of a Z gradient primary coil shown in FIG. 9A;

FIG. 9C shows a chart of axial position current paths for a half of the embodiment of a Z gradient primary coil shown in FIG. 9A;

FIG. 10A shows a simplified layout of an embodiment of a Z gradient shield coil;

FIG. 10B shows a cross sectional view an embodiment of a conductor used with the embodiment of a Z gradient shield coil shown in FIG. 10A;

FIG. 10C shows a chart of axial position current paths for a half of the embodiment of a Z gradient shield coil shown in FIG. 10A.

DETAILED DESCRIPTION

Figure 1:
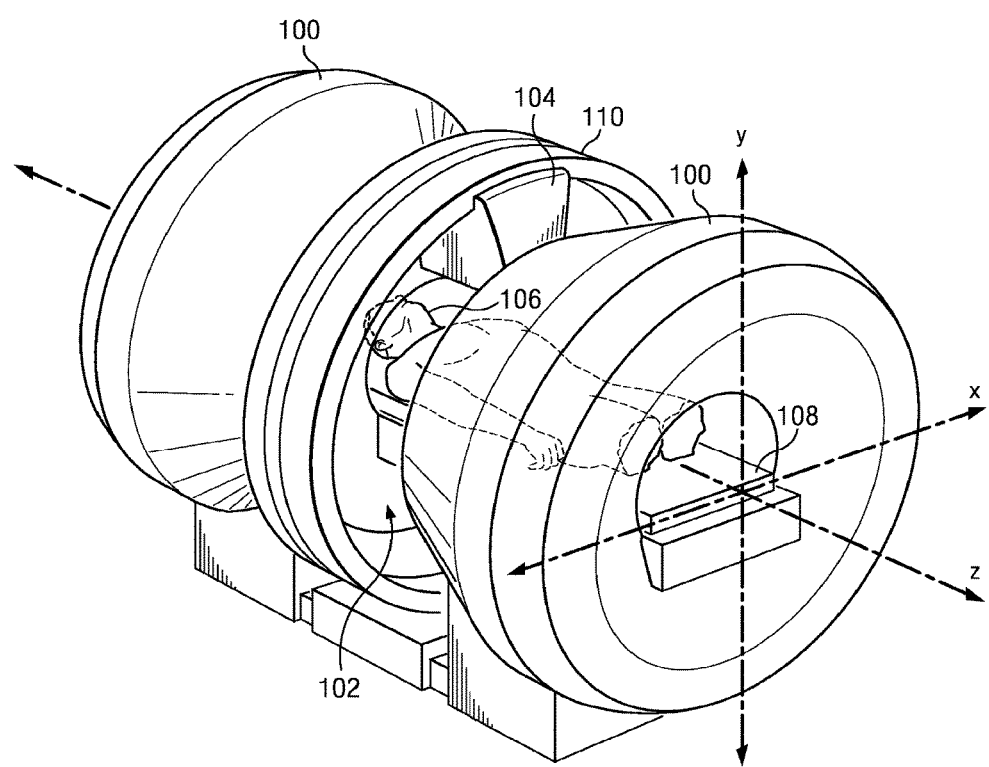
FIG. 1 shows a perspective view of a horizontal open MRI with an instrument located in its center gap region, as can be used with some embodiments of the present disclosure.

The gradient coil assembly of the present disclosure may be used with any type of horizontal magnetic resonance imaging (MRI) system. It is particularly well suited for use with a split solenoid or horizontal "open" MRI that includes a gap between two horizontal MRI magnet halves. The gradient coil assemblies disclosed herein are further well suited for use with a horizontal open MRI that is used with an additional medical instrument being operated within its gap. FIG. 1 depicts such an arrangement with a horizontal open MRI 100 having a gap region 102. An instrument 104 is mounted in the gap region 102 on a gantry 110. Also depicted are a patient 106 and patient couch 108. In some embodiments, the gantry 110 can be used to reposition the instrument 104 about the patient 106 (i.e., about the Z-axis shown in FIG. 1).

The embodiment of FIG. 1 can include elements of a system of the assignee of the current application, ViewRay, Inc., described, in part, in U.S. Patent Application Publication 2005/0197564 to Dempsey, titled "System for Delivering Conformal Radiation Therapy while Simultaneously Imaging Soft Tissue" (hereafter "Dempsey '564"), which is hereby incorporated by reference. For example, the instrument 104 can comprise a radiation therapy device and associated multi-leaf collimator (MLC), which, in combination with a fast-imaging horizontal open MRI, allows for improved radiation therapy that accounts for target location during treatment, as discussed in Dempsey '564. While only a single assembly is shown as the instrument 104 in FIG. 1, some embodiments can include multiple assemblies associated with instrument 104. For example, some embodiments may include three radiation head assemblies (not shown in FIG. 1) mounted in gap 102, distributed about the Z-axis, and rotatable about the Z-axis on the gantry 110. While some aspects of the embodiments disclosed herein are described with respect to the ViewRay system disclosed by Dempsey '564, such aspects are not required for use with the disclosed gradient coil assembly. It is contemplated that the gradient coil assembly disclosed herein may be used in any type of MRI, with or without the use of an associated instrument 104. Furthermore, for systems utilizing an instrument 104, such instruments are not limited to radiation therapy devices such as radiation sources, or a LINAC, but can include any type of instrument used with an MRI.

Figure 2:
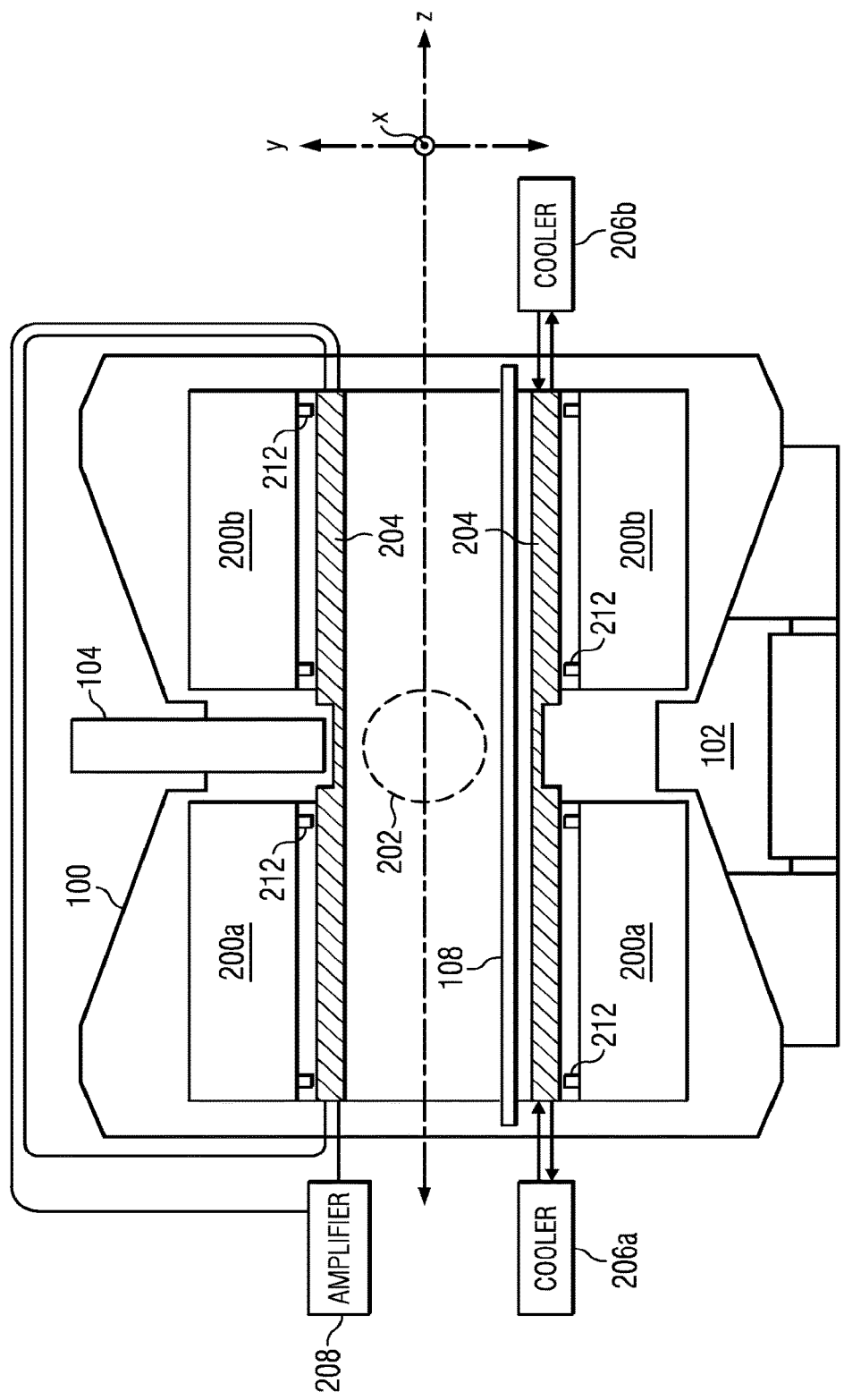
FIG. 2 shows a simplified cross-sectional view of some embodiments of the system shown in FIG. 1.

FIG. 2 is diagrammatic cross-section of the system shown in FIG. 1. The embodiment of FIG. 2 depicts a horizontal open MRI 100 including a pair of main magnets 200a and 200b, separated by gap 102. The MRI is used to image a region of interest 202 above patient couch 108. The MRI 100 can include additional conventional components not shown, for example, an RF system, including RF coils, and potentially one or more shim coils. The coordinate system used in the figures and throughout this disclosure refers to the longitudinal axis through the MRI bore as the Z-axis. The X-axis extends perpendicular to the Z-axis and from side to side of the MRI 100; the Y-axis extends perpendicular to the Z-axis and from the bottom to the top of MRI 100.

An embodiment of the gradient coil assembly 204 disclosed herein is depicted in FIG. 2 along with its associated coolers 206a,b and amplifier 208, described in detail below. In this embodiment, the gradient coil assembly 204 is supported by mounts 212 that may be located both at the outer ends of the main magnets, as well as near the MRI gap. Exemplary mounts are vibration isolating devices such as the IsoDamp® C1002 sold by E-A-R Specialty Composites, a division of Aearo Technologies. Gradient coil assembly 204 may be directly mounted to main magnets 200a,b. However, electrical currents in gradient coil assembly 204 in the presence of the main magnetic field (generated by main magnets 200a, b) create torques, forces, and vibrations that can drive vibration and heat into main magnets 200a,b and increase boil-off. Inclusion of mounts 212 both at the outer and gap ends of main magnets 200a,b can provide for improved vibration isolation and reduce the unsupported span of gradient coil assembly 204.

Figure 3:
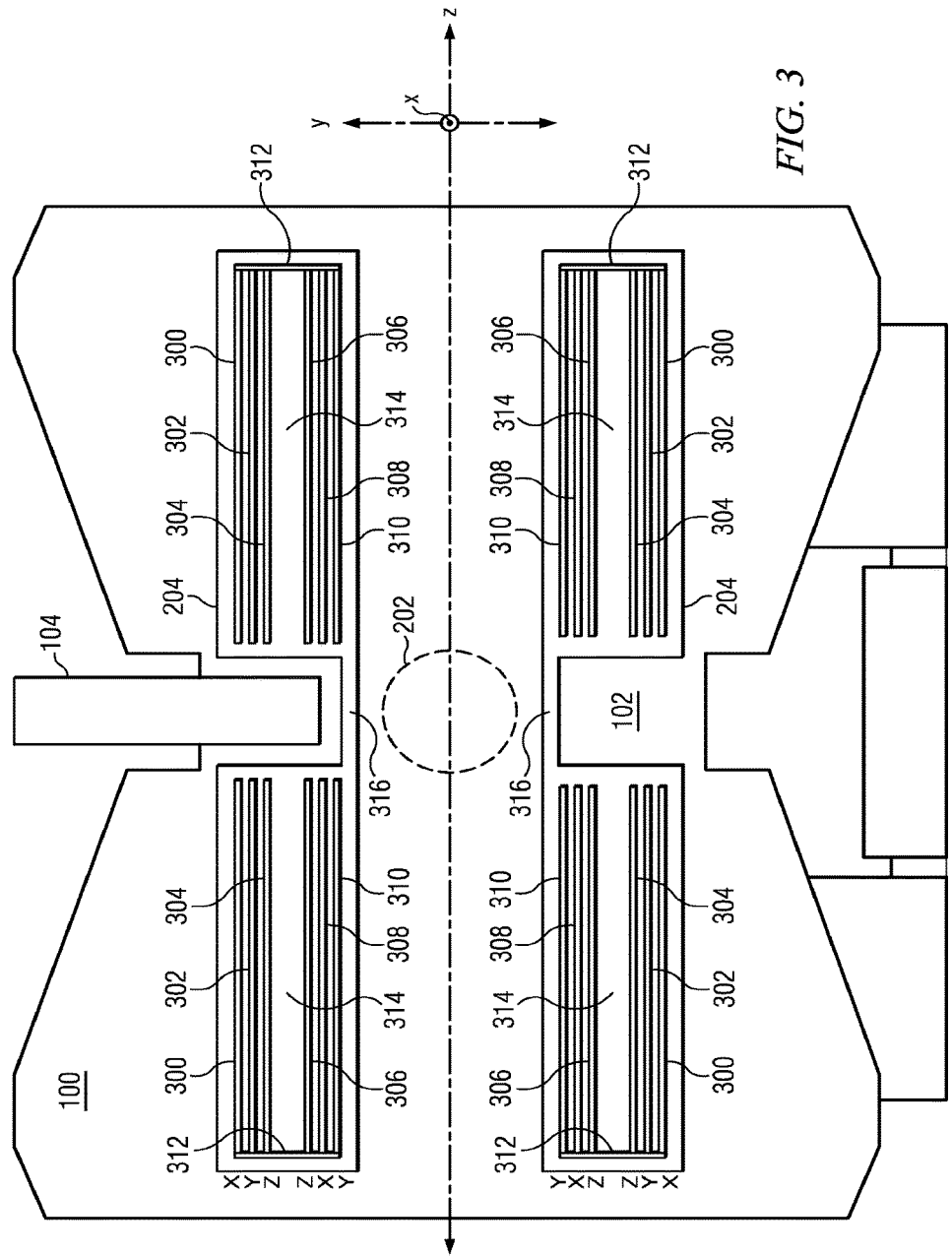
FIG. 3 shows a simplified and expanded cross-sectional view of some embodiments of the gradient coil assembly shown in FIG. 2.

FIG. 3 shows an expanded, more detailed cross-sectional diagram of an embodiment of gradient coil assembly 204. This embodiment of gradient coil assembly 204 contains X, Y, and Z shield coils (300, 302, 304 respectively) and Z, X and Y primary gradient coils (306, 308, 310 respectively). The embodiment also contains connections 312 between each of the respective coil pairs (connecting X shield coil 300 to X primary coil 310, Y shield coil 302 to Y primary coil 308, and Z shield coil 304 to Z primary coil 306) located at the outer ends of gradient coil assembly 204 (away from the gap 102). The coils 300-310 are disposed within a supporting structure 314, which may be made from a material such as an epoxy resin.

As an example, in some implementations of this embodiment, the inner diameter of the gradient coil assembly 204 can be about 800 mm and the outer diameter can be about 1044 mm, in combination with an MRI 100 having a gap 102 that is approximately 200 mm wide and where the length between the outer ends of the gradient coil assembly 204 is about 2190 mm. These dimensions are provided merely as an example and should not be considered limiting, as the dimensions may vary.

The disclosed gradient coil assembly 204 may be formed as two separate halves, so as to leave the gap 102 open for uninhibited physical access to the patient 106. Such an open configuration allows for use with an additional instrument 104, for example, a radiation treatment system. However, it is not necessary for the gap 102 to remain completely open, as long as any obstruction does not result in excessive attenuation of, for example, a radiation beam that may be emitted from instrument 104. In the present embodiment, the gradient coil assembly 204 is of singular construction, having a gap portion 316 of supporting structure 314. The gap portion 316 traverses the gap 102 and is a thin, uniform structure constructed for uniform and minimal radiation attenuation (for example, less than 5% attenuation in the case where a 60Co γ-ray source is used). In the preferred embodiment, gap portion 316 is a portion of a continuous inner former that can be made from material that is stable in the radiation environment, for example, an epoxy-fiberglass or epoxy-carbon fiber structure. Its thickness can be, for example, approximately 5 mm, and its density can be, for example, less than or equal to 2 g/cm3. One advantage of this continuous structure is that opposite sides of gradient coil assembly 204 are naturally aligned, eliminating troublesome two-part gradient alignment issues and associated asymmetric eddy currents and imaging fields. Another advantage of the instant embodiment is improved mechanical damping and support, mechanically balancing and stabilizing the forces and torques experienced by the gradient coils in operation. It is contemplated that gap portion 316 can be provided with access ports cut into it or can be removed after the installation of gradient coil assembly 204.

Figure 4:
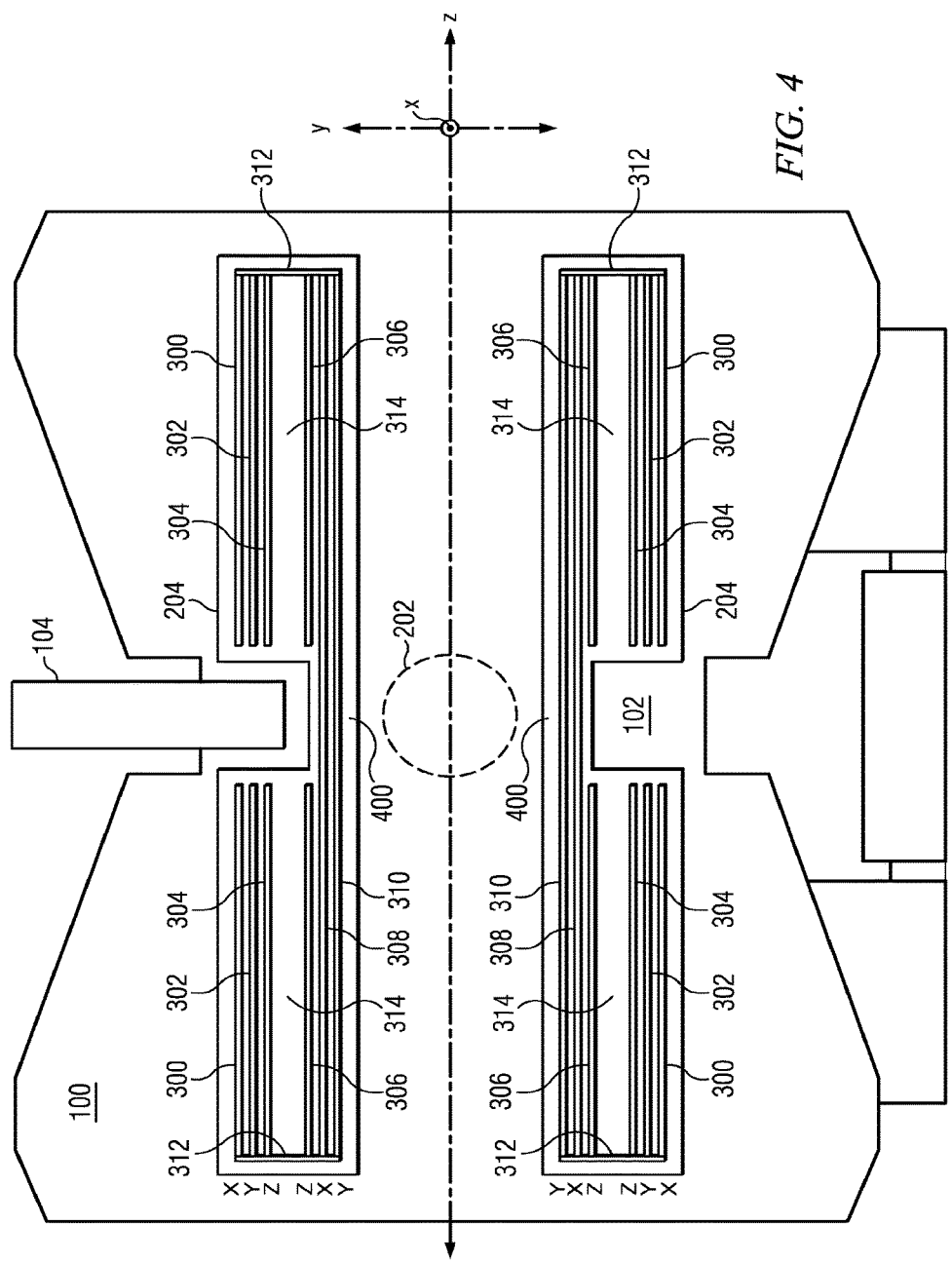
FIG. 4 shows a simplified and expanded cross-sectional view of an alternative embodiment of the gradient coil assembly shown in FIG. 2.

FIG. 4 depicts an alternative embodiment for the gap portion of supporting structure 400, which contains gradient coils traversing the gap 102. Z gradient coils are naturally gapped, but in this embodiment, primary X and Y coils 308 and 310 can be continuous across the gap 102 and can be made, for example, from aluminum (e.g., sheet coils or wound conductors directly cooled). Aluminum is an example of a conductor with lower density than copper and will thus be beneficial in applications where the gradient coil assembly is used with an instrument 104 delivering radiation therapy to region 202. An important aspect of this embodiment is that supporting structure 400 has a radiation attenuation that matches the attenuation of the included conductors, so that attenuation will be consistent across the structure. In the case of aluminum coils, supporting structure 400 could include an epoxy-filament wound tube with, for example, glass or carbon filaments and appropriate fillers such as alumina between the coils. The uniform attenuation of this alternative design will facilitate accurate radiation delivery and dose calculations.

The alternative embodiment of FIG. 4 will have greater beam attenuation (for the case including a radiation therapy device as instrument 104) due to its increased thickness and inclusion of gradient coils. However, this embodiment has the advantage of increasing the usable field of view of the MRI because it will not experience the loss of linearity of gradient field strength associated with a split design and will avoid the problem of radial rollover of the transverse gradient fields.

Turning now to FIGS. 5-10, and with reference to FIG. 3, specific embodiments of the gradient and shield coils will be explained in greater detail. The present embodiment is described with reference to a horizontal open MRI having an instrument 104 employed in the gap, although it is understood that many aspects of the disclosure may be applied to single magnet MRIs used without associated instruments. The instrument 104 of the present example can be, for example, the radiation therapy device previously discussed, although it is understood that many other treatment or imaging modalities may be used with the present disclosure such as biopsy needles, ablation devices, surgical devices, ultrasound, PET, SPECT, CT, LINAC and others.

The radiation device of the present example comprises three equally spaced Cobalt 60 heads with associated multi-leaf collimators (MLCs), for example, as disclosed in Dempsey '564 and incorporated herein by reference. The MLCs are typically composed of computer-controlled tungsten leaves that shift to form specific patterns, blocking portions of the radiation beams and shaping them according to a predetermined treatment plan. These MLCs are preferably placed close to or within gap 102 and are typically made of tungsten with aluminum housings, both conductive materials. When such materials are placed in the vicinity of the time varying currents of gradient coil assembly 204, eddy currents will be induced in them. Eddy currents induced in instrument 104 will result in power dissipation in the device and can also interfere with imaging. In the case of MLCs, heat may cause thermal expansion of individual leaves and interfere with their operation. Other instruments including conductive materials that may be used with the disclosed system would be faced with similar problems.

The presently disclosed gradient coil assembly 204 reduces these issues, in part, by moving common concentrations of conductors away from the gap 102. For example, gradient-to-shield interconnects in horizontal split gradients are typically located adjacent the radial surfaces of the gradient coil assemblies facing the gap 102. However, the presently disclosed gradient coil assembly 204 moves such connectors 312 away from the gap 102. For example, the connectors may be preferably spaced at least 50 mm from gap 102, although the present disclosure contemplates that the connectors may be closer than 50 mm from the gap 102. In the embodiments depicted in FIGS. 3 and 4, the connections 312 are located at the outer edges of gradient coil assembly 204. Moving concentrations of current created by radially oriented conductors away from the gap 102 will reduce eddy currents induced in any instrument 104. In addition, concentrations of longitudinally oriented conductors or loops are minimized near the gap 102 and the eyes of fingerprint coils are preferably located at least 50 mm from gap 102. Furthermore, while prior horizontal split magnet gradient coils have included radially oriented loops along the region of gap 102, the present disclosure preferably moves any such radially oriented conductors at least 50 mm from gap 102. In the exemplary embodiments disclosed in FIGS. 5-10, the gradient and shield coils are substantially cylindrical in shape. While a cylindrical shape is preferred, the disclosed coils can be other shapes that do not result in additional conductor and current concentrations near the gap 102.

Figure 5A:
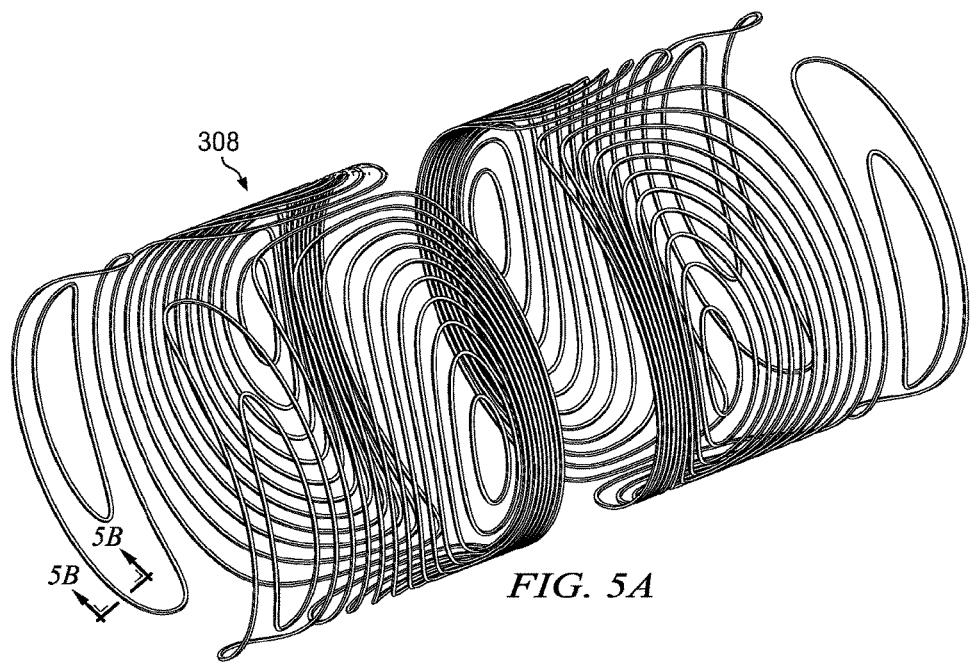
FIG. 5A shows a simplified layout of an embodiment of an X gradient primary coil.
Figure 5B:
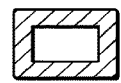
FIG. 5B shows a cross sectional view an embodiment of a conductor used with the embodiment of an X gradient primary coil shown in FIG. 5A.
Figure 5C:
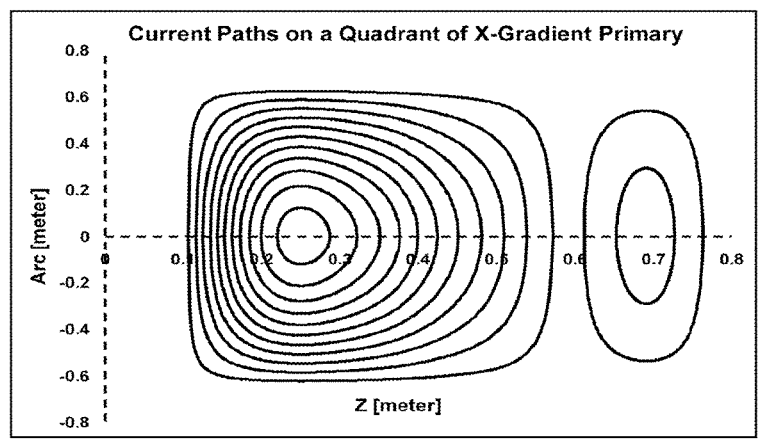
FIG. 5C shows a chart of current paths for an unfolded single quadrant of the embodiment of an X gradient primary coil shown in FIG. 5A.
Figure 6A:
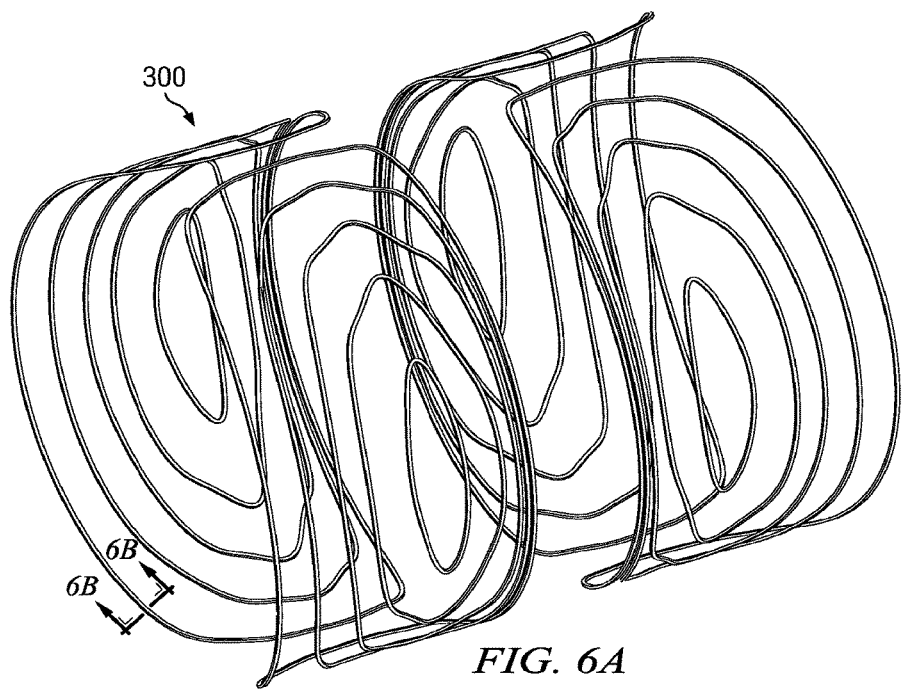
FIG. 6A shows a simplified layout of an embodiment of an X gradient shield coil.
Figure 6B:
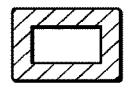
FIG. 6B shows a cross sectional view an embodiment of a conductor used with the embodiment of an X gradient shield coil shown in FIG. 6A.
Figure 6C:
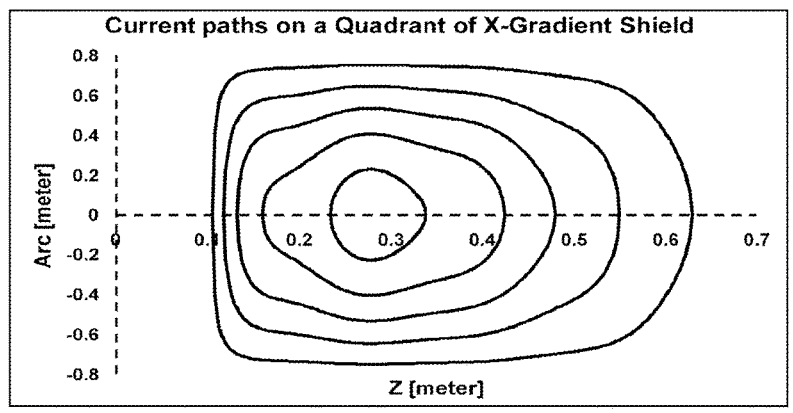
FIG. 6C shows a chart of current paths for an unfolded single quadrant of the embodiment of an X gradient shield coil shown in FIG. 6A.
Figure 7A:
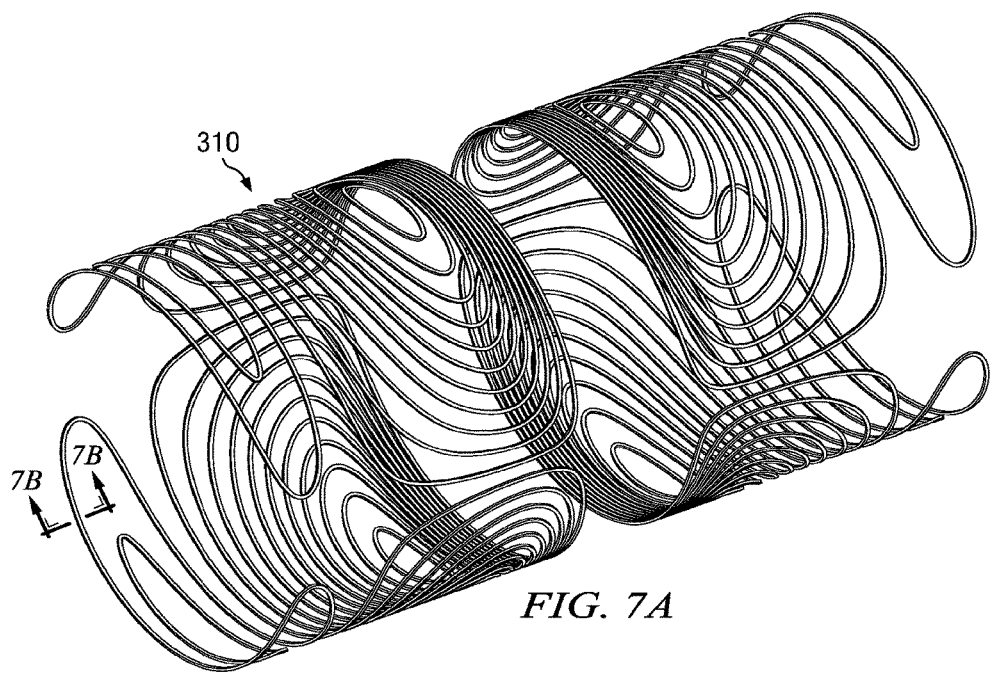
FIG. 7A shows a simplified layout of an embodiment of a Y gradient primary coil.
Figure 7B:
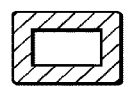
FIG. 7B shows a cross sectional view an embodiment of a conductor used with the embodiment of a Y gradient primary coil shown in FIG. 7A.
Figure 7C:
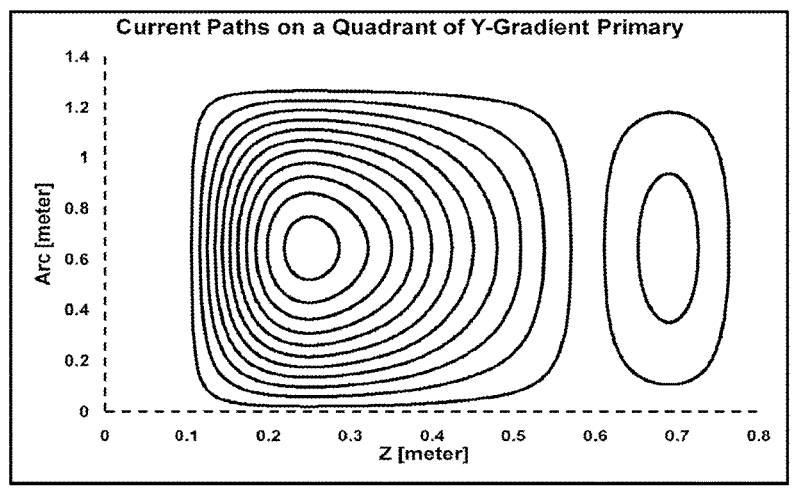
FIG. 7C shows a chart of current paths for an unfolded single quadrant of the embodiment of a Y gradient primary coil shown in FIG. 7A.
Figure 8A:
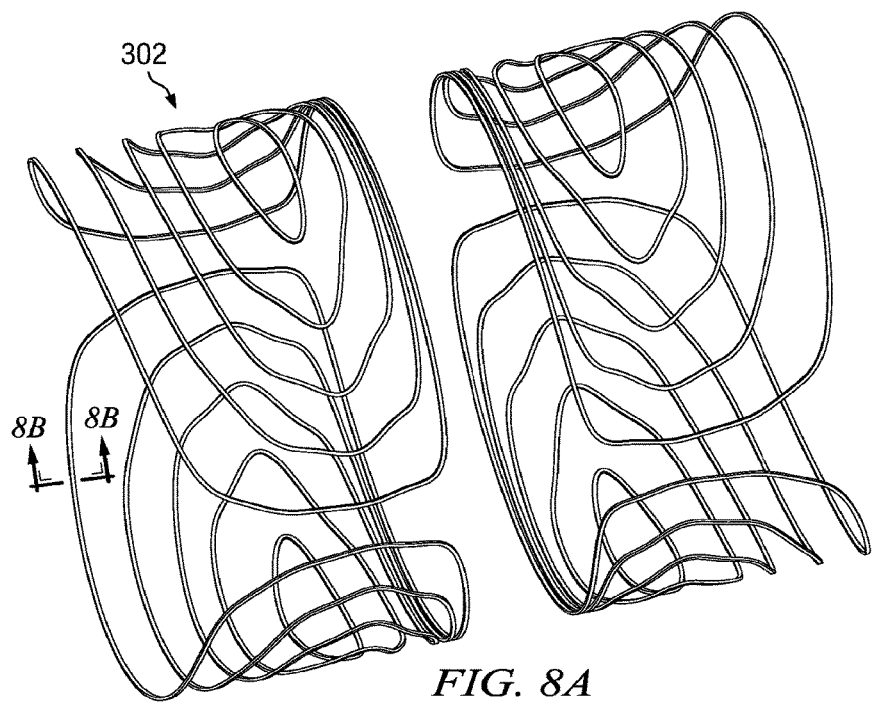
FIG. 8A shows a simplified layout of an embodiment of a Y gradient shield coil.
Figure 8B:
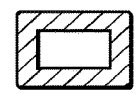
FIG. 8B shows a cross sectional view an embodiment of a conductor used with the embodiment of a Y gradient shield coil shown in FIG. 8A.
Figure 8C:
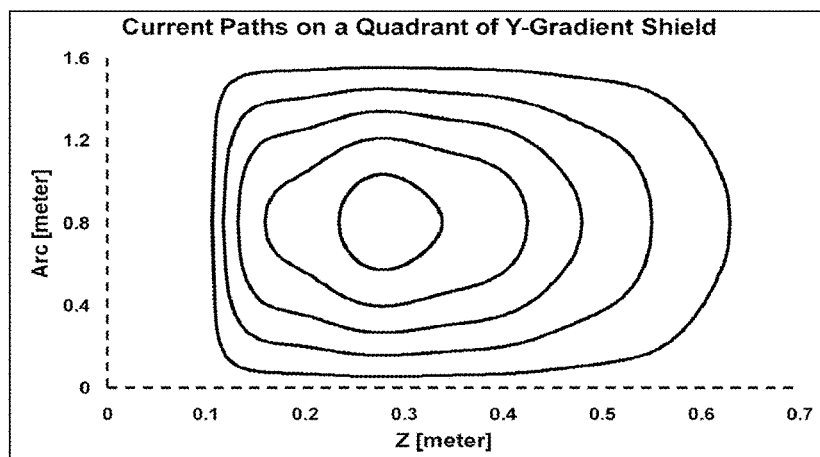
FIG. 8C shows a chart of current paths for an unfolded single quadrant of the embodiment of a Y gradient shield coil shown in FIG. 8A.

Referring now to the exemplary X gradient primary coil 308 depicted in FIG. 5A, the coil includes 11 forward and 2 reverse turns in each of its identical quadrants. The connections between turns (for example, juggles) are not depicted as is common in the art. The centroids of the current paths (all single turns) are shown in FIG. 5C. The X gradient primary coil 308 includes reverse turns at its ends away from gap 102 to compensate for thrust and torque forces. Among other things, this compensation reduces forces on the thin, continuous gap portion of supporting structure 316 (or 400) described as part of this embodiment. The Y gradient coil 310 similarly includes 11 forward and 2 reverse turns as shown in FIGS. 7A and 7C. The shield coils for both the X and Y gradients (300 and 302) of this embodiment include 5 turns in each of their identical quadrants as shown in FIGS. 6A, 6C, 8A, and 8C. The Z-gradient primary coil (306) of this embodiment has 42 total turns as shown in FIGS. 9A and 9C and the Z gradient shield coil has 28 total turns as shown in FIGS. 10A and C. Additional parameters for some implementations of the exemplary coils discussed herein are detailed in Table 1 below.

TABLE 1

Example Coil Characteristics

| Property | X Gradient | Y Gradient | Z Gradient |
|---|---|---|---|
| Mean radius (Primary) [mm] | 414.31 | 408.21 | 421.86 |
| Mean radius (Shield) [mm] | 516.45 | 510.35 | 502.80 |
| Conductor Thickness [mm] | 7 mm × 5.1 mm hollow conductor | 7 mm × 5.1 mm hollow conductor | 8 mm × 8 mm hollow conductor |
| Number of Turns (Primary) | 11 fwd/2 rev (per quadrant) | 11 fwd/2 rev (per quadrant) | 28 (total) |
| Number of Turns (Secondary) | 5 (per quadrant) | 5 (per quadrant) | 28 (total) |
| Total Electrical Coil Length (Primary) [mm] | 1533.81 | 1533.81 | 1407.38 |
| Total Electrical Coil Length Secondary [mm] | 1274.74 | 1264.74 | 1533.80 |
| DC Resistance (Primary) [mΩ] | 68.29 | 68.28 | 52.98 |
| DC Resistance (Secondary) [mΩ] | 33.18 | 33.18 | 42.09 |
| DC Resistance (Total) [mΩ] | 101.47 | 101.46 | 95.07 |
| Inductance [μH] | 227.10 | 224.38 | 356.325 |
| Non-Linearity [%] over ±17.5 cm/ ±25 cm/±30 cm | +2.81/−3.23/ −21.69 | +2.37/−5.2/ −25.46 | −4.14 |
| Non-Uniformity [%] over ±17.5 cm | −33.35 | −32.89 | −11.0 |

TABLE 1-continued

Example Coil Characteristics

| Property | X Gradient | Y Gradient | Z Gradient |
|---|---|---|---|
| Radial Rollover | | | |
| Z = 0.0 mm | 27.7 cm | 27.1 cm | No rollover |
| Z = 25 mm | 28.0 cm | 27.4 cm | |
| Z = 50 mm | 30.0 cm | 29.7 cm | |
| Z = 75 mm | 34.1 cm | 33.6 cm | |
| Z = 100 mm | No rollover | No rollover | |
| Gradient Strength [mT/m] | 16.0 | 16.0 | 16.0 |
| Current [A] for G = 16 mT/m | 528.93 | 510.40 | 356.29 |
| Sensitivity [μT/m/A] | 30.25 | 31.348 | 44.91 |
| Slew rate [mT/m/ms] at G = 16 mT/m and V = 1800 V | 228.44 | 237.00 | 227.76 |
| Rise Time [μs] | 76.82 | 73.24 | 78.71 |
| Net Thrust Force [N] at G = 16 mT/m | 6.92 | 4.64 | 2.34 |
| Net Torque on each half [N*m] at G = 16 mT/m | 79.6 | 72.43 | 0.0 |
| Eddy Current Effect (50 cm DSV) | <1.0% | <1.0% | <0.5% |
| Eddy Current Effect Variation (50 cm DSV) | 0.42% | 0.42% | 0.23% |

To meet performance specifications on the order of those in Table 1, including a 16 mT/m gradient strength and slew rate of approximately 200 mT/m/ms, a current driver with high voltage and current capability is desirable. In the instant embodiment, gradient coil assembly 204 can be driven with an amplifier 208 such as a Siemens SQ gradient amplifier capable of delivering 650A maximum current and 2000V maximum voltage, although other amplifiers or multiple amplifiers could be used. The high current and current densities existing in the coils of the present disclosure are preferably cooled by direct cooling through the core of each coil. The instant embodiment employs separate coolers (206a and 206b) at each end of MRI 100 and each primary and shield coil is made with a hollow core as shown in cross section FIGS. 5B, 6B, 7B, 8B, 9B and 10B. The dimensions of the X and Y primary and shield coil cross sections in this embodiment can be the same, for example with a 7 mm by 5.1 mm width and height, and a 4.6 mm by 2.6 mm center lumen. The dimensions of the exemplary Z primary and shield coils can be, for example, 8 mm by 8 mm with a 6 mm diameter center lumen. While direct cooling can be used in the present example, other methods of cooling known in the art, such as indirect cooling, or a combination of direct and indirect cooling, may be used.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A gradient coil assembly for use with a magnetic resonance imaging system (MRI), wherein the MRI has a longitudinal axis and a gap, and a radiation device produces a radiation beam aimed orthogonally to the longitudinal axis and through the gap, the gradient coil assembly comprising:
   a plurality of primary gradient coils, wherein at least one of the primary gradient coils that traverses the gap of the MRI and has a first radiation attenuation value; and
   a supporting structure containing the at least one of the primary gradient coils, the supporting structure having a portion that traverses the gap, the portion further comprising a filler causing the portion to have a second radiation attenuation value substantially equivalent to the first radiation attenuation value such that attenuation of the radiation beam will be substantially uniform as it passes through the portion and the at least one of the primary gradient coils that traverses the gap.

2. The gradient coil assembly of claim 1, further comprising:
   a plurality of shielding coils disposed within the portion; and
   electrical connections between the primary gradient and shielding coils arranged so that the electrical connections are located a sufficient distance from the gap to reduce eddy currents induced in the radiation device.

3. The gradient coil assembly of claim 2, wherein the electrical connections between the primary gradient and shielding coils are located at least 5 centimeters from the gap.

4. The gradient coil assembly of claim 1, wherein one or more of the primary gradient coils are formed as substantially cylindrical conductors about the longitudinal axis.

5. The gradient coil assembly of claim 1, wherein one or more of the primary gradient coils is directly cooled.

6. The gradient coil assembly of claim 5, wherein one or more of the primary gradient coils comprises a hollow conductor.

7. The gradient coil assembly of claim 6, further comprising two cooling units.

8. The gradient coil assembly of claim 2, wherein the MRI has outer ends and the electrical connections between the primary gradient and shielding coils are located substantially at the outer ends of the MRI.

9. The gradient coil assembly of claim 1, wherein the at least one primary gradient coil traversing the gap is aluminum.

10. A gradient coil assembly for use with a magnetic resonance imaging system (MRI), wherein the MRI has a longitudinal axis a gap, and a radiation device produces a radiation beam aimed orthogonally to the longitudinal axis and through the gap, the gradient coil assembly comprising:
    a plurality of primary gradient coils, wherein at least one of the primary gradient coils is continuous across the gap of the MRI and has a first radiation attenuation value; and
    a supporting structure containing the at least one of the primary gradient coils, the supporting structure having a portion that traverses the gap, the portion further comprising a filler causing the portion to have a second radiation attenuation value substantially equivalent to the first radiation attenuation value such that the supporting structure has a radiation attenuation that is consistent across the supporting structure.

11. The gradient coil assembly of claim 10, further comprising:
    a plurality of shielding coils disposed within the supporting structure portion; and
    electrical connections between the primary gradient and shielding coils arranged so that the electrical connections are located a sufficient distance from the gap to reduce eddy currents induced in the radiation device.

12. The gradient coil assembly of claim 11, wherein the electrical connections between the primary gradient and shielding coils are located at least 5 centimeters from the gap.

13. The gradient coil assembly of claim 10, wherein one or more of the primary gradient coils are formed as substantially cylindrical conductors about the longitudinal axis.

14. The gradient coil assembly of claim 10, wherein one or more of the primary gradient coils is directly cooled.

15. The gradient coil assembly of claim 14, wherein one or more of the primary gradient coils comprises a hollow conductor.

16. The gradient coil assembly of claim 15, further comprising two cooling units.

17. The gradient coil assembly of claim 11, wherein the MRI has outer ends and the electrical connections between the primary gradient and shielding coils are located substantially at the outer ends of the MRI.

18. The gradient coil assembly of claim 10, wherein the at least one primary gradient coil traversing the gap is aluminum.

19. A gradient coil assembly for use with a magnetic resonance imaging system (MRI), wherein the MRI has a longitudinal axis and a gap, and a radiation device produces a radiation beam aimed orthogonally to the longitudinal axis and through the gap, the gradient coil assembly comprising:
    a plurality of primary gradient coils, wherein at least one of the primary gradient coils that traverses the gap of the MRI and has a first radiation attenuation value; and
    a supporting structure containing the at least one of the primary gradient coils, the supporting structure having a portion that traverses the gap and the portion also having a filler causing a second radiation attenuation value such that attenuation of the radiation beam is consistent as it passes through the supporting structure portion and the at least one of the primary gradient coils that traverses the gap.

20. The gradient coil assembly of claim 19, wherein the at least one primary gradient coil traversing the gap is aluminum.

* * * * *